Oct. 2, 1962 F. D. AVIS Plant Pat. 2,179
APPLE TREE
Filed Nov. 7, 1961
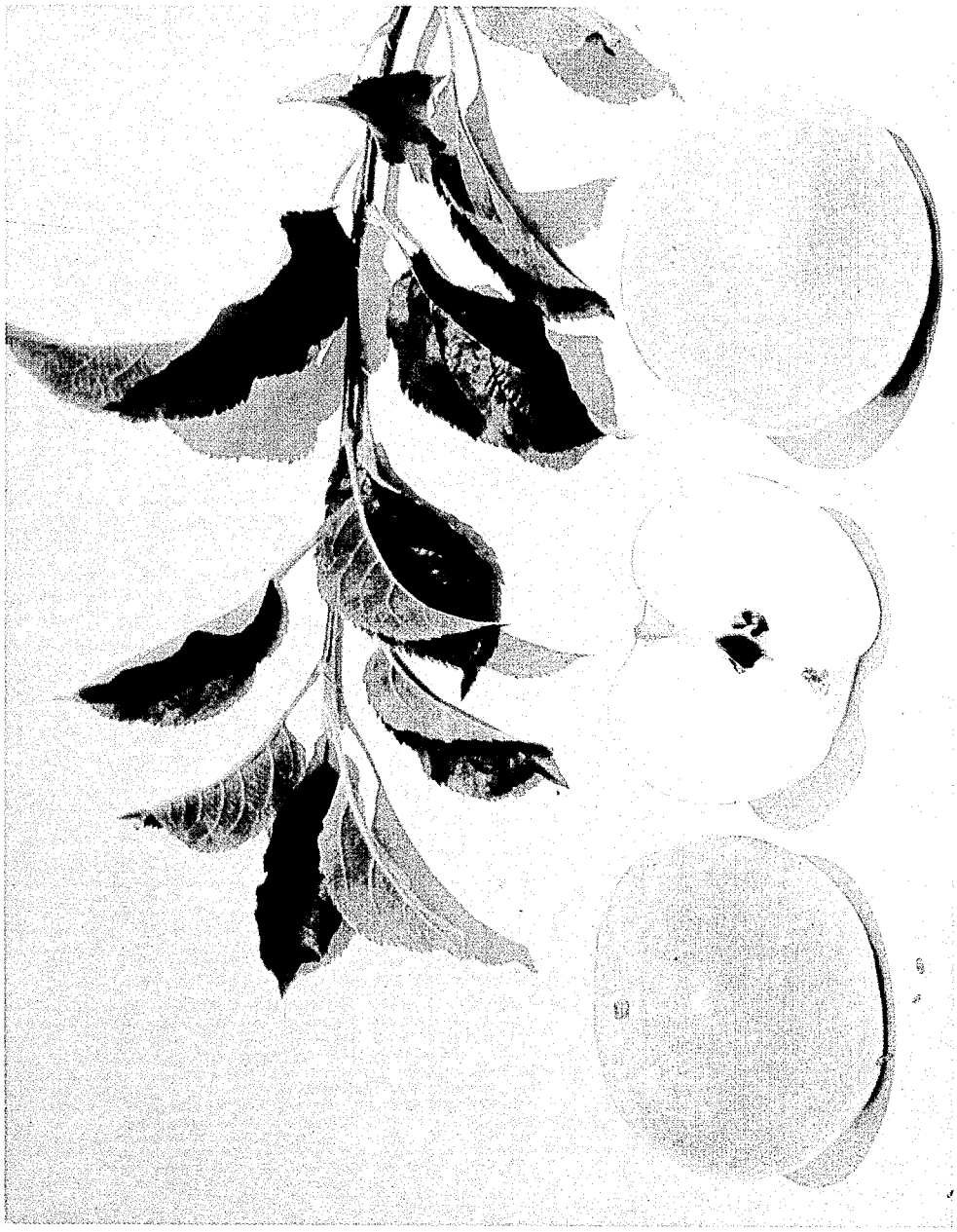
INVENTOR
Floyd D. Avis
BY Robb & Robb
ATTORNEYS United States Patent Office Plant Pat. 2,179
Patented Oct. 2, 1962

2,179
APPLE TREE

Floyd D. Avis, Clarklake, Mich., assignor to Stark Bro's Nurseries & Orchards Company, Louisiana, Mo., a corporation of Missouri Filed Nov. 7, 1961, Ser. No. 150,841
1 Claim. (Cl. 47—62)

The present invention relates to a new and distinct variety of apple tree which was discovered by me as a sprout from a newly found seedling root which had been accidentally cut off by a mower while mowing operations were being conducted on my cultivated orchard property in Jackson County, Michigan.

At the time of my discovery aforesaid, I was growing various fruit trees on my orchard property located in Jackson County, Michigan, and while engaging in mowing operations, my attention was attracted to a sprout from a seedling root of a tree which had been accidentally cut off by the mower. As a matter of interest, I left the young sprout to continus its growth and come into fruiting. As the result, I found when the sprout matured that the tree bore fruit of a shape and size resembling that of the fruit of the well known McIntosh variety (unpatented) but that the color of the fruit was yellow, with a Scarlet blush resembling the fruit color of the variety "Maiden Blush" (unpatented). However, the fruit was found to have a much better flavor, and the trees were much more productive, with the fruit ripening about the same season as "Maiden Blush," but about two weeks earlier than "McIntosh."

Although the parentage of my newly found seedling is not definitely known, I am convinced that the seedling represents a new and distinct variety, as evidenced by the foregoing outstanding characteristics which differentiate it from any other variety of which I am aware.

Asexual reproduction of my new variety, as performed by grafting near Louisiana, in Pike County, Missouri, shows that the foregoing characteristics and distinctions come true and are established and transmitted through succeeding propagagations.

The accompanying drawing shows typical specimens of the fruit and foliage of my new variety as depicted in color as nearly true as it is reasonably possible to make the same in a color illustration of this character, certain of said fruit specimens being shown in elevation, and one of said fruit specimens being shown in cross-section.

The following is a detailed description of my new variety, with color terminology in accordance with Ridgway's Color Standards and Nomenclature (hereinafter abbreviated as "Ridgway") and the Horticultural Colour Guide (hereinafter abbreviated as "HCG"), as indicated, except where general color terms of ordinary dictionary significance are obvious:

(Observations made from specimens grown in Pike County, Missouri.)

Dates first and last pickings: About August 18 and about August 25, respectively.

Tree: Medium large; vigorous; spreading; dense; round-topped; rapid growing; hardy; very productive; regular bearing.

*Trunk.*—Medium stocky; smooth.

*Branches.*—Medium thick; smooth; much-branched.

Color—Deep Olive, Plate XL, Colour No. 21''', tone *k* (Ridgway).

*Lenticels.*—Few; medium small.

*Leaves.*—Medium small; medium width; medium length; oval; abruptly pointed; thick; rugose. Length—3½ inches. Width—2 inches. Color—Parsley Green, Plate 00962, page 193, vol. 2 (HCG). Margin—coarsely serrate. Petiole—long (about 1 1/16 inches); medium thick.

Flowers: Medium early in comparison with other varieties; medium large size.

*Date of first bloom.*—About April 26.

*Date of full bloom.*—About May 3.

*Color.*—White.

Fruit:

*Maturity when described.*—Eating ripe (about August 25).

*Size.*—Variable. Axial diameter—2½ inches. Transverse diameter—from 3 inches to 3½ inches.

*Form.*—Oblate at base; angular.

*Cavity.*—Symmetrical at base; flaring toward apex; undulate. Depth—½ inch. Breadth—1⅛ inches. Markings—color—Pod Green, Plate 061/2, page 120, vol. 2 (HCG).

*Basin.*—Symmetrical; abrupt at base; medium wide; undulate; pubescent. Depth—7/16 inch. Breadth—1 inch. Markings—none.

*Stem.*—Stout; pubescent. Length—7/16 inch. Breadth—3/16 inch.

*Calyx.*—Closed; segments persistent; broadly lanceolate; about 5/16 inch long; imbricate at base; ascending; reflexed from base to apex; both outer and inner surfaces pubescent.

*Skin.*—Thin; tough; smooth; glossy; waxed. Dots—conspicuous; few; small; even; ruptured; circular; color—Primose Yellow, Plate 601/3, page 65, vol. 1 (HCG); distribution—extend from basin to cavity, but most numerous toward basin. Ground color—Primose Yellow, Plate 601/3, page 65, vol. 1 (HCG). Color markings—blushed; bright; color—Scarlet, Plate 19/1, page 19, vol. 1 (HCG).

*Bloom.*—Wanting.

*Scarfskin.*—Wanting.

*General color effect.*—Creamy yellow, with about 40% of surface bright light red.

*Flesh.*—Juicy. Color—white, with yellowish tint. Texture—firm; tender; fine; crisp. Flavor—mild; sprightly; rich. Aroma—wanting. Quality—good.

*Core.*—Distant. Bundle area—small; orbicular; symmetrical at base. Halves of core—equal. Bundles—inconspicuous; in 2 whorls. Core lines—clasping; indistinct in cross-section. Carpellary area—indistinct. Calyx tube—pubescent; cone-shaped; entire depth ¼ inch. Styles—present; united toward base; pubescent toward base. Stamens—in one distinct whorl; median. Seed cells—open. Longitudinal section—broadly oval; obtuse at apex; surface fissured.

Seeds:

*Number.*—8 or 9 perfect, and 1 imperfect; usually 2 per cell.

*Length.*—⅜ inch.

*Breadth.*—3/16 inch.

*Form.*—Acute.

*Color.*—Prout's Brown, Plate XV, Colour No. 15′, tone M (Ridgway).

Keeping quality: Medium; about 15 days in ordinary storage.

I claim:

A new and distinct variety of apple tree, substantially as herein shown and described, characterized particularly as to novelty by the unique combination of a fruit shape and size generally resembling that of the "McIntosh" variety (unpatented), but having a fruit color that is generally yellow with a Scarlet blush and resembling the color of the fruit of the "Maiden Blush" variety (unpatented), said fruit being of better flavor, and the trees being more productive than "Maiden Blush," with the fruit ripening at about the same season as "Maiden Blush" and about two weeks earlier than "McIntosh."

No references cited.